(12) United States Patent
Janetzko et al.

(10) Patent No.: US 9,915,648 B2
(45) Date of Patent: Mar. 13, 2018

(54) METHOD FOR ANALYZING A SAMPLE

(75) Inventors: Alfred Janetzko, Butzbach (DE);
Wilhelm Sänger, Wilnsdorf (DE);
Cyril E. Geacintov, Mountainside, NJ (US)

(73) Assignee: DRG INSTRUMENTS GMBH, Marburg (DE)

( * ) Notice: Subject to any disclaimer, the term of this patent is extended or adjusted under 35 U.S.C. 154(b) by 0 days.

(21) Appl. No.: 13/817,259

(22) PCT Filed: Aug. 5, 2011

(86) PCT No.: PCT/EP2011/063511
§ 371 (c)(1),
(2), (4) Date: Mar. 4, 2013

(87) PCT Pub. No.: WO2012/022631
PCT Pub. Date: Feb. 23, 2012

(65) Prior Publication Data
US 2013/0183694 A1    Jul. 18, 2013

(30) Foreign Application Priority Data
Aug. 16, 2010   (DE) .................. 10 2010 037 009

(51) Int. Cl.
*G01N 33/53* (2006.01)
*G01N 35/10* (2006.01)
*G01N 35/04* (2006.01)

(52) U.S. Cl.
CPC ............. *G01N 33/53* (2013.01); *G01N 35/10* (2013.01); *G01N 2035/0436* (2013.01)

(58) Field of Classification Search
CPC ... G01N 2035/0439; G01N 2035/0443; G01N 2035/0446; G01N 2035/0441
See application file for complete search history.

(56) References Cited

U.S. PATENT DOCUMENTS 4,346,056 A    8/1982   Masahiko
5,468,453 A *  11/1995  Holt et al. ................... 422/509
(Continued)

FOREIGN PATENT DOCUMENTS

DE    30 308 79 A1    2/1981
DE    33 185 73 A1    1/1984
(Continued)

OTHER PUBLICATIONS

Harris, Quantitative Chemical Analysis, sixth edition. New York: W. H. Freeman; Company (2003), p. 414.*

*Primary Examiner* — Christine Foster
*Assistant Examiner* — Ellen J Marcsisin
(74) *Attorney, Agent, or Firm* — Fox Rothschild LLP

(57) ABSTRACT

The invention relates to a method of analysing a sample, comprising the analysis of clinical-chemical parameters and the analysis of immunodiagnostic parameters in a fully automatic analysis apparatus, wherein the analysis apparatus comprises a pipetting apparatus, at least one holder for a reagent cartridge containing the components necessary for carrying out the analysis, a holding apparatus for a measurement cell, at least one measurement cell, with each reagent cartridge being associated with a measurement cell, a holding apparatus for a sample container containing sample, and a photometric or spectrometric measurement device. On the basis of a sample it is possible here for a plurality of different clinical-chemical and/or immunodiagnostic parameters to be determined, to which end a dedicated reagent cartridge is inserted into a holding apparatus of the analysis apparatus for each clinical-chemical or immunodiagnostic parameter to be determined.

6 Claims, 3 Drawing Sheets

(56) References Cited

U.S. PATENT DOCUMENTS

Figure 1A:
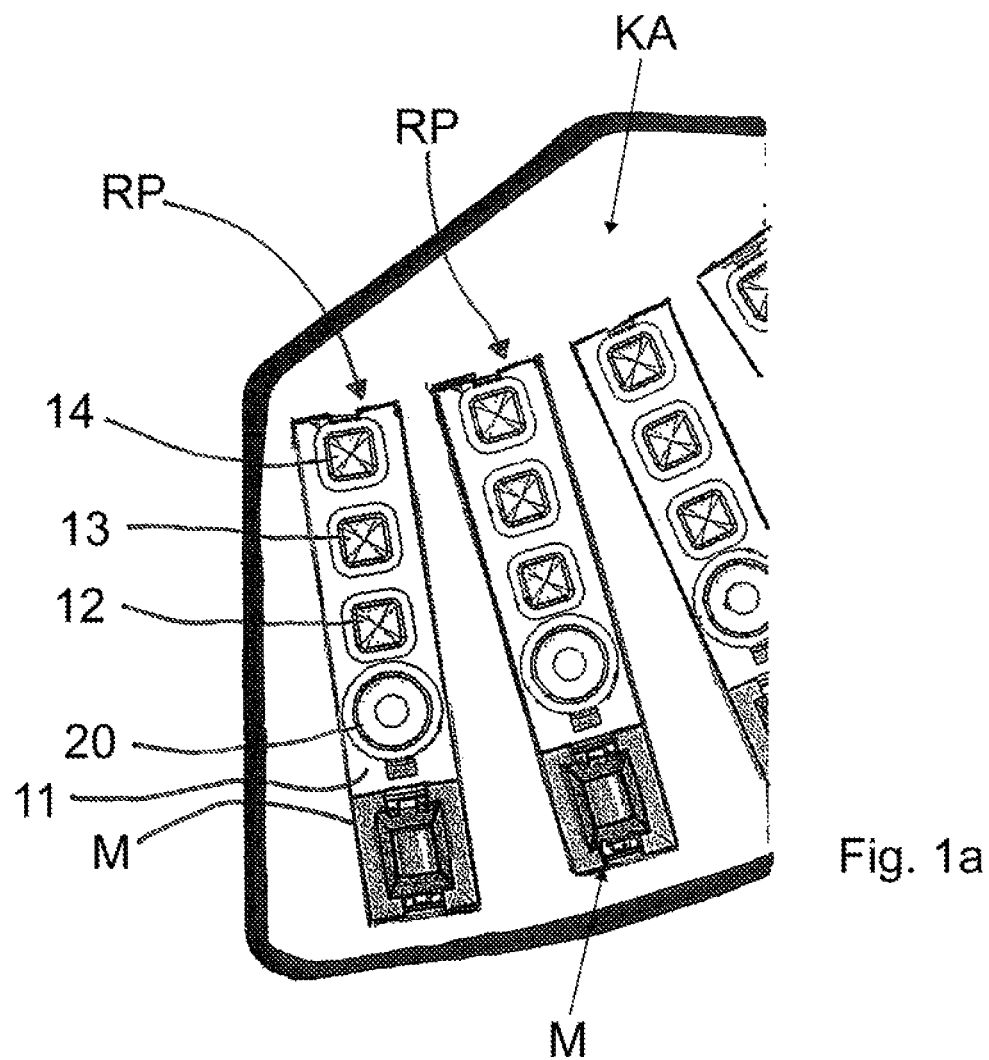

| | | | |
|---|---|---|---|
| 5,482,861 A * | 1/1996 | Clark et al. | 436/48 |
| 5,538,849 A * | 7/1996 | Uematsu et al. | 435/6.19 |
| 5,597,702 A * | 1/1997 | Wong et al. | 435/18 |
| 6,107,082 A | 8/2000 | Bajard | |
| 6,485,980 B1 | 11/2002 | Adolfsen et al. | |
| 6,752,960 B1 | 6/2004 | Matsubara et al. | |
| 6,943,030 B2 | 9/2005 | Gebrian et al. | |
| 2003/0202905 A1 | 10/2003 | Devlin et al. | |
| 2005/0013737 A1 | 1/2005 | Chow et al. | |
| 2006/0292038 A1 * | 12/2006 | Johansson et al. | 422/82.05 |
| 2007/0253866 A1 | 11/2007 | Rousseau | |

FOREIGN PATENT DOCUMENTS

| | | |
|---|---|---|
| DE | 39 37 609 A1 | 5/1991 |
| DE | 198 07 177 A1 | 9/1999 |
| DE | 198 57 215 A1 | 6/2000 |
| DE | 10 2004 034 801 A1 | 3/2006 |
| DE | 10 2004 047 822 A1 | 4/2006 |
| DE | 102009051428 A1 * | 5/2011 |
| EP | 216 026 A1 | 4/1987 |
| EP | 0216026 A1 | 4/1987 |
| EP | 2 073 017 A1 | 6/2009 |
| EP | 2073017 A1 | 6/2009 |
| JP | 2006220494 A | 8/2006 |

\* cited by examiner

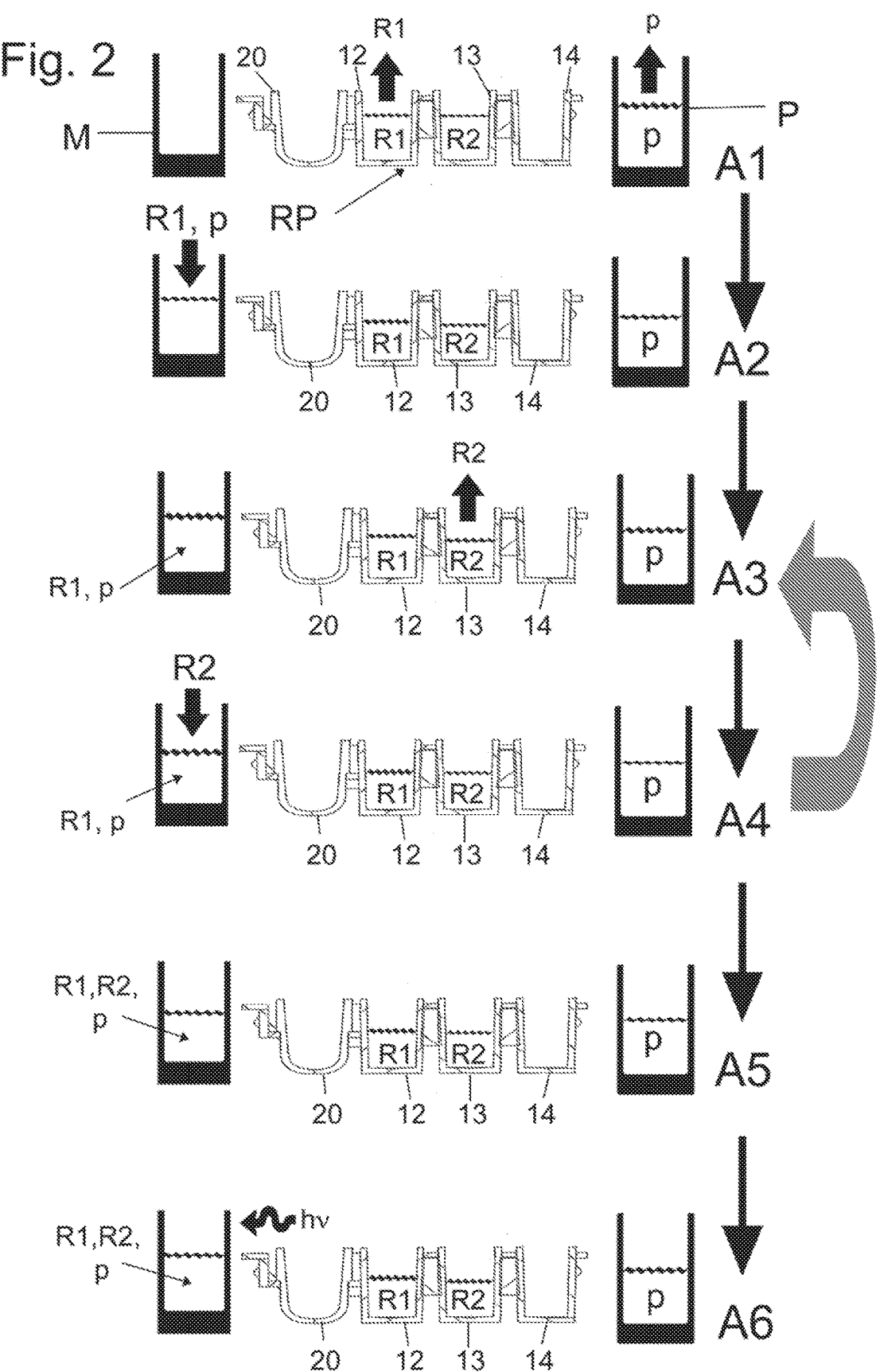

METHOD FOR ANALYZING A SAMPLE

This application is a U.S. National Phase Application of International Application No. PCT/EP11/063511 filed 5 Aug. 2011, which claims priority to DE Application No. 102010037009.6 filed 16 Aug. 2010, the disclosures of which are hereby incorporated by reference in their entirety.

The invention relates to a method for analyzing a sample according to the preamble of claim 1.

Analysis methods to determine clinical chemistry parameters and analysis methods to determine immunodiagnostic parameters in medical samples are generally known. Customarily the clinical chemistry parameters are determined in a first procedure and the immunodiagnostic parameters in an additional procedure, with a separate analytical device—usually fully automatic—used for each procedure.

For small laboratories or medical practices this especially has a drawback in that at least two automatic analysis devices must be procured and maintained: a first to carry out the clinical chemistry test, which normally is done at body temperature, i.e., 37° C., and a second to make the immunodiagnostic determinations—usually at room temperature, i.e., 21° C. It is not merely the acquisition of these that is expensive, but rather two devices always need to be serviced. The reason this is necessary is the differing detection procedures according to which clinical chemistry parameters and those of immunodiagnosis are determined.

Therefore, the task of the invention is make available a method, with the aid of which it is possible to measure both clinical chemistry parameters and immunodiagnostic parameters from a single sample in one and the same automatic analysis device. The method should be able to implemented simply and in as cost-effective a manner as possible.

The main features of the invention are provided in the characterizing parts of claims 1 and 12. Embodiments are the subjects of claims 2 to 11 and 13 to 15.

In a procedure for analyzing a sample, including analysis of clinical chemistry parameters and analysis of immunodiagnostic parameters in a fully-automatic analysis device, wherein the analysis device contains a pipetting device, at least one holder for a reagent cartridge which contains the necessary components to carry out the analysis, a holding apparatus for a measurement cell, at least one measurement cell, wherein one measurement cell is assigned to each reagent cartridge, a holding apparatus for a sample container comprising a sample and a photometric or spectrometric measuring device, the invention makes provision that the method includes these steps:
 a) Insertion of reagent cartridges for the analyses to be carried out into the holding apparatus
 b) Insertion of the sample container containing sample into the sample device
 c) Determining clinical chemistry parameters with the aid of that measurement cell to which the reagent cartridge is assigned, which is provided to carry out the analysis of the particular clinical chemistry parameters, and/or
 d) determination of the immunodiagnostic parameters with the aid of that measurement cell to which the reagent cartridge is assigned, which is provided to carry out the analysis of the particular clinical chemistry parameters
 e) cleaning or removal of the used measurement cells
 f) removal of the used reagent cartridges and the sample container It is perceived that the invention-specific method thus in essence consists of the following three procedural steps:
 Preparation of the analysis device
 Determination of the desired clinical chemistry and/or immunodiagnostic parameters
 Dissemination of the data and cleaning of the analysis device The "preparation of the analysis device" aspect summarizes steps a) and b); the "determination of the desired clinical chemistry and/or immunodiagnostic parameters" aspect summarizes steps c) and d), and the "dissemination of the data and cleaning of the analysis device" aspect summarizes steps e) and f) of the above-named method.

It is perceived that the special advantage of the method resides in the fact that in one and the same method, both the clinical chemistry parameters and the immunological components of a sample can be determined. Therefore, it is no longer necessary to provide different equipment for analysis of clinical chemistry parameters and immunodiagnostic parameters. For smaller medical practices especially, this represents an enormous cost saving. This special advantage derives from both the clinical chemistry parameters and the immunodiagnostic parameters being determined with the aid of one measurement cell. In contrast, with all the traditional methods, only the clinical chemistry parameters can be measured with a measurement cell; the immunodiagnostic parameters, however, are measured in a well of a microtitration plate.

A further advantage of the invention-specific method is that for evaluation both of clinical chemistry parameter and immunodiagnostic parameters, only a single photometric unit needs to be present in the analysis device. At the same time, thanks to the invention-specific method, it is possible that in one and the same analysis device from one sample, multiple different clinical chemistry and/or immunodiagnostic parameters are determined. Therefore, for example, to make a diagnosis, a doctor can follow this procedure: first he takes a sample of the body fluids to be studied from a patient. Then he selects various reagent cartridges, depending on which parameters he wishes to determine. For each of the parameters, he inserts the corresponding reagent cartridges into the analysis device and thus starts the invention-specific process. As described above, this provides him in a single procedural pass with the desired various clinical chemistry and immunodiagnostic parameters, on the basis of which he then can make his diagnosis.

It is perceived that it is advantageous if, for each clinical chemistry or immunodiagnostic parameter, a separate reagent cartridge is inserted into a holding apparatus for a reagent cartridge of the analysis device. In the particular reagent cartridges, the necessary documenting reagents for the particular test are contained in recesses. Therefore, it is appropriate that with the aid of the invention-specific method, from one sample multiple different clinical chemistry and/or immunodiagnosis parameters are determined. It makes sense that for each clinical chemistry or immunodiagnostic parameter to be determined, a separate reagent cartridge is inserted in a holding apparatus for a reagent cartridge of the analysis device, with the necessary documenting reagents for the particular tests contained in recesses in the particular reagent cartridges.

It is favorable if the reagent cartridges that serve for analysis of the clinical chemistry parameters, contain at least one documenting reagent and if the reagent cartridges that serve for analysis of the immunodiagnostic parameters contain a recess with a conjugant, and a second recess with a substrate solution and a solid phase.

According to the invention, the clinical chemistry parameters are determined by the following steps:

a) Taking of a documenting reagent from the reagent cartridge and taking of the sample with the aid of the pipetting device
b) Releasing the documenting reagent and the sample from the pipetting device into the measurement cell assigned to the reagent cartridge
c) Incubation of the documenting reagent with the sample, with the documenting reagent reacting with the clinical chemistry parameters present in the sample and to be documented, into a product that can be documented photometrically
d) Photometric determination of the concentration of the product in the measurement cell with the aid of the measuring device.

Alternatively, the clinical chemistry parameters can also be determined in the following steps:
a) Taking of a first documenting reagent from a first recess of the reagent cartridge and taking of the sample with the aid of a pipetting device
b) Releasing the documenting reagent and the sample from the pipetting device into the measurement cell assigned to the reagent cartridge
c) Taking a second documenting reagent from another recess in the reagent cartridge with the aid of the pipetting device
d) Releasing the second documenting reagent from the pipetting device into the measurement cell
e) Incubating the documenting reagent with the sample, with the documenting reagent reacting with the clinical chemistry parameters present in the sample to a product that can be photometrically documented
f) Photometric determination of the concentration of the product in the measurement cell with the aid of the measuring device.

These two versions are carried out especially if more than one reagent is necessary to determine the specific clinical chemistry parameter.

It is also conceivable that the clinical chemistry parameters are determined using the following steps:
a) Taking of a first documenting reagent from a first recess of the reagent cartridge and taking of the sample with the aid of the pipetting device
b) Releasing the documenting reagent and the sample from the pipetting device into the measurement cell assigned to the reagent cartridge
c) Taking of a second documenting reagent from another recess in the reagent cartridge with the aid of the pipetting device
d) Releasing the second documenting reagent from the pipetting device into the measurement cell
e) Taking of at least one additional documenting reagent from an additional recess in the reagent cartridge or from a recess in an additional reagent cartridge and releasing the additional documenting reagent or reagents into the measurement cell
f) Incubating the documenting reagents with the sample, with the documenting reagent reacting with the clinical chemistry parameters present in the sample and to be documented, to a product that can be photometrically documented
g) Photometric determination of the concentration of the product in the measurement cell with the aid of the measuring device.

To obtain as error-free a result as possible, it is favorable if the concentration of the product of the documenting reaction is photometrically determined by the following steps:

Conducting a first photometric measurement in the measurement cell with the aid of the measuring device
Incubating the mixture of the first and/or second documenting reagent and sample in the measurement cell
Conducting a second photometric measurement in the measurement cell with the aid of the measuring device.

Especially thereby, measurement inaccuracies are prevented and compensated for, which may arise if the reaction has not absolutely completely finished at the time of the first measurement.

According to the invention, the immunodiagnostic parameters are determined by the following steps:
a) Taking of conjugate from a first recess of the reagent cartridge provided for carrying out the immunodiagnostic analysis and taking of a sample via the pipetting device
b) Releasing the conjugate and sample from the pipetting device to the solid phase of the reagent cartridge
c) Incubating the solid phase with conjugate and sample
d) Removal of excess conjugate and sample by washing the solid phase
e) Taking of substrate solution from a second recess of the reagent cartridge provided for carrying out the immunodiagnostic analysis via the pipetting device
f) Releasing the substrate solution from the pipetting device to the solid phase
g) Incubating the substrate solution on the solid phase
h) Taking of the converted substrate solution via the pipetting device
i) Releasing the converted substrate solution from the pipetting device into the measurement cell
j) Measuring the concentration of the converted substrate in the substrate solution with the aid of the measuring device.

Steps a) to g) correspond to the generally customary steps for carrying out an ELISA. This means that when the conjugate and sample are jointly released to the solid phase, the immunological parameter to be determined, for example a specific peptide, binds an antibody or another protein to its binding partner coupled on the solid phase—thus a corresponding antibody, a suitable antigen, or something similar. The conjugate contains a suitable enzyme complex which consists of a binding partner and an enzyme coupled to the binding partner. The binding partner likewise binds to the parameter to be documented. In this way, the entire complex of parameters, binding partners and enzymes are immobilized on the solid phase. Excess complex and excess sample are removed or washed out in the next step. The substrate solution then added contains an enzyme-specific substrate thus immobilized on the solid phase. This is converted by a reaction with the enzyme, through which the color is changed and also a defined change is evoked in optical density at a certain wavelength.

The specific advantage of the invention-specific method now consists in the enzyme-substrate reaction having been ended in that the complete substrate solution, which now contains both converted and non-converted substrate, is removed from the solid phase and re-pipetted for evaluation in a measurement cell. In this way it is possible, with an arrangement of reagent cartridge and measurement cell that always remains the same, to determine a plurality of different parameters—primarily both immunodiagnostic and clinical chemistry ones. In a sequence always remaining the same, the concentration of the corresponding parameter can be determined with the aid of the measurement cell and a single photometric unit.

Another particular advantage of this method in this connection is that it is not necessary to provide a stopping solution as an additional component, which otherwise would be customary to put a defined end to the enzyme-substrate reaction. Rather, this is completed here simply by removal and re-pipetting of the partially converted substrate solution into the measurement cell. Since the enzymes immobilized on the solid phase remain on the solid phase and are not carried along into the measurement cell, the substrate is not further converted as soon as the solution is removed from the solid phase.

A further advantage of the invention-specific method is that the method can be carried out at a temperature between 27° C. and 39° C., preferably at a temperature of 37° C. This invention-specific and special adaptation of the temperature conditions of the ELISA test makes it possible to determine the clinical chemistry parameters and the immunodiagnostic parameters, one immediately after the other, in whatever sequence, without having to change the temperature of the device used for the analysis, which otherwise would have involved long heating and cooling phases and corresponding waiting times.

To prevent contamination of the tip of the pipetting device and thus a falsification of the analysis results, it is favorable if, after release of the documenting reagent, the sample, conjugate or substrate solution, the tip of the pipetting device is changed or cleaned at a washing station.

Advantageously the invention also makes provision for a method to determine immunological parameters via ELISA in a fully-automated analysis device, wherein the analysis device comprises a pipetting device, at least one holder for a reagent cartridge which contains the required components for carrying out the analysis, a holding apparatus for a measurement cell, at least one measurement cell, with each reagent cartridge assigned to a measurement cell, a holding apparatus for a sample vessel, and a photometric or spectrometric measuring device, the method comprising these steps:

a) Taking of the conjugate and sample via the pipetting device
b) Release of the conjugate and sample from the pipetting device to the solid phase
c) Incubation of the solid phase with conjugate and sample,
d) Removal of excess conjugate and sample by washing of the solid phase
e) Taking of substrate solution via the pipetting device
f) Release of substrate solution from the pipetting device to the solid phase
g) Incubation of the substrate solution in the solid phase
h) Taking of the converted substrate solution via the pipetting device
i) Release of the converted substrate solution from the pipetting device into the measurement cell
j) Measuring the concentration of the converted substrate in the substrate solution with the aid of the measuring device.

It is favorable if the conjugate and the sample are mixed after release into the solid phase. It is also advantageous if the concentration is measured by determining the optical density at various wavelengths and if, prior to taking of the sample via the pipetting device in step a), the sample is diluted in a separate dilution cartridge.

Figure 1B:
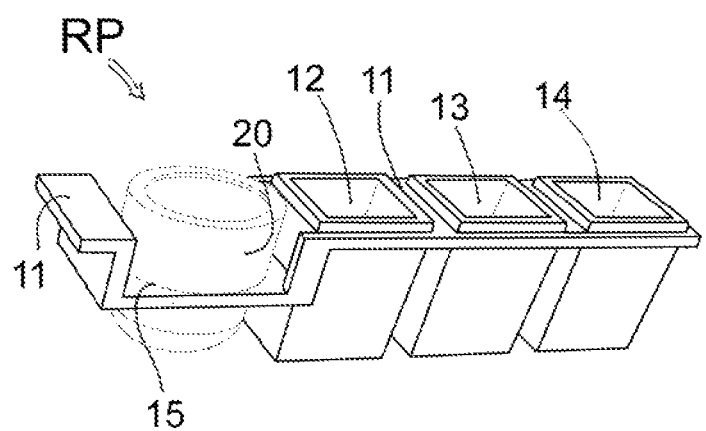
Figure 3:
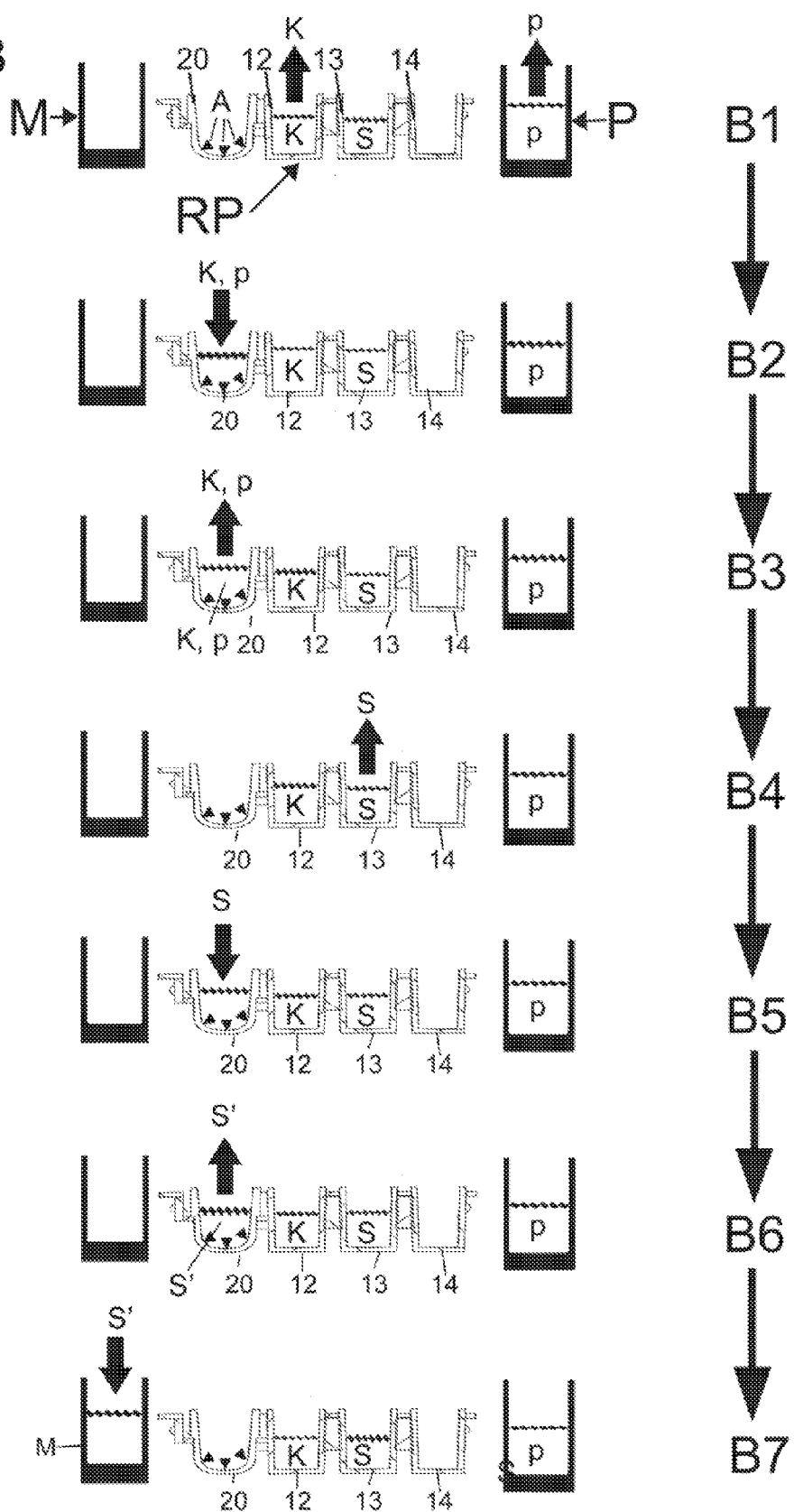

Further features, particulars and advantages of the invention are derived from the wording of the claims as well as from the following specification of embodiment examples using the drawings. Shown are:

FIG. 1a Arrangement of several selected reagent cartridges and measurement cells for determining multiple factors in a fully automated device for conducting the invention-specific method FIG. 1b View of a reagent cartridge that is used to carry out the invention-specific method FIG. 2 Testing sequence to determine a clinical chemistry parameter during the carrying out of the invention-specific method FIG. 3 Testing sequence to determine an immunodiagnostic parameter during the carrying out of the invention-specific method As already described above, in essence the invention-specific method comprises the following three steps:

Preparation of the analysis device
Determination of the desired clinical chemistry and/or immunodiagnostic parameters
Dissemination of the data and cleaning of the analysis device Customarily, taking of the sample precedes the method. Additionally, the user must determine which parameter he would like to detect, i.e., investigate in the sample p taken. If this has happened, then the analysis device can be prepared.

This methodological step comprises the insertion of the appropriately selected reagent cartridge RP, as well if necessary as the insertion of the measurement cell M and insertion of the sample P into the analysis device. The reagent cartridges RP are then selected according to which parameters are to be determined. In the analysis device, the measurement cells can either be fixedly installed, or disposable cells can be used. It is also especially advantageous if the method is carried out with a device in which the sample p is inserted into the device separately from the reagent cartridges RP and the measurement cells M.

One can perceive in FIG. 1a how the reagent cartridges RP and measurement cells M are inserted, one behind the other, in a carousel KA of an analysis device. Each reagent cartridge RP has a measurement cell M assigned to it.

As is perceptible in FIG. 1b, each of the reagent cartridges RP consists of a housing 11, in which three recesses 12, 13, 14 are formed. In these recesses 12, 13, 14, depending on the parameters to be determined, the appropriate reagents or solutions for carrying out the particular test are contained.

Additionally, in the housing 15 a recess 15 is formed, into which a solid phase 20 is inserted. To solid phase 20, an appropriate antigen or antibody A can be coupled, if the reagent cartridge RP is provided to carry out an immunodiagnostic test. It is especially advantageous in this regard if the method is carried out with a device in which the sample p or the sample container P containing sample p is inserted into the device separately from the reagent cartridges RP and measurement cells M.

If the analysis device has been appropriately prepared, then the user can input into the computer controlling the device the sequence in which he has inserted the appropriate reagent cartridges into the device and thus the sequence of the parameters to be determined. True, it is conceivable that, for example, the reagent cartridges RP are provided with a bar code or something similar, so that the device can independently detect the parameters to be determined.

The device independently determines the desired clinical chemistry and/or immunodiagnostic parameters after the analysis device has been made ready in the procedural step which follows—namely, determining the desired clinical chemistry and/or immunodiagnostic parameters. First, the first reagent cartridge RP is started up, and a determination made of whether, with its aid, a clinical chemistry parameter or an immunodiagnostic one is to be determined. Then, with the aid of an appropriate test, the desired parameter is determined, as described in what follows.

If the parameter to be determined is a clinical chemistry factor, then the testing sequence schematically depicted in FIG. 2 and described as follows is carried out. Before the start of the sequence, the sample p is already present in sample holder P. Depending on the need, in recesses 12, 13, 14, the reagent cartridge RP contains one or more documenting reagents R1, R2.

In a first step A1, from the pipetting device (not shown) a first documenting reagent R1 is taken and a corresponding amount of sample p is taken.

For this, first the document reagent R1, which has been prepared in one of the recesses 12, 13, 14 of reagent cartridge RP is taken in by suction. Then an air bubble is admitted, both to avoid contamination of the sample p present in sample container P and to prevent direct mixing of documenting reagent R1 and sample p until the next step. Then lastly, sample p is admitted.

In a second step A2, the admitted documenting reagent R1 and the sample p are released to measurement cell M of the analysis device. Then document reagent R1 and sample p are mixed there. Understandably, this mixing can also be actively supported by intake and withdrawal pipetting or something similar.

If another documenting reagent R2 is need for the selected test, then in a third step A3 this is taken up from another recess 12, 13, 14 of reagent cartridge RP, and in a fourth step A4 also released to measurement cell M. Then again the already present fluids are mixed.

As needed, steps A3 and A4 are repeated until all of the necessary components are present in measurement cell M.

Before the test is evaluated, the components R1, R2, p mixed in measurement cell M are incubated in another step A5 for a defined period. The time depends on the reaction proceeding during the test, and can be either already programmed or inputted by the user.

In the last step, A6, a photometric evaluation is carried out. For this, the optical density is determined by fluoroscopy of measurement cell M with light at a specific wavelength hv—for example, 420 nm—immediately after the end of the incubation time. This can be followed by a second measurement following another defined incubation period. The actual value which the test result depicts, is then determined by comparison of the two measured values and a reference which is pre-programmed or individually determined by the user.

If the parameter to be determined is an immunodiagnostic parameter, then the test sequence depicted in FIG. 3 is followed, namely an ELISA, is carried out as follows.

In a first step B1, a solution contained in the reagent cartridge RP, which contains enzyme conjugate and is designated as conjugate K for short, is taken jointly with a corresponding amount of sample p. Sample p, as before, is made ready in sample container P. The taking up is done analogous to step A1, i.e., first conjugate K is taken up from the appropriate recess 12 of reagent cartridge RP, and then an air bubble, and lastly the sample p from sample container P.

In a second step B2, conjugate K and sample p are released to the solid phase 20 of reagent cartridge RP, and there incubated for a certain duration. An antigen or antigen body A suitable for the parameter to be documented is coupled to the solid phase 20.

During the incubation time, the parameter to be documented binds to the antigen or antibody A coupled to the solid phase 20, and simultaneously to a binding partner contained in conjugate K (not shown). This binding partner is in turn coupled with an enzyme. In this way, a complex is immobilized on the solid phase 20 of reagent cartridge RP. Along with the binding partner and the bound antigen and antibody A, this complex comprises the parameter to be documented and an enzyme which is in a position to convert a specific substrate.

In a third step B3, excess conjugate K and excess sample p are then removed by washing out solid phase 20.

In the next step, B4, substrate solution S is taken from another recess 13 in reagent cartridge RP. This substrate solution S contains a substrate specially adjusted to the enzyme contained in conjugate K, in a previously defined concentration. If the substrate—TMB, for example (others are possible)—is converted by the enzyme, then a specifically documentable color change takes place.

Substrate solution S is released in step B5 to solid phase 20. Now the substrate contained in the solution can be converted by the enzyme previously immobilized in the solid phase 20. With this, both the converted and the unconverted substrate remain mobile in the solution, but the enzyme complex remains bound to the solid phase. The converted substrate solution S' thus produced now contains, depending on the amount of the enzyme immobilized in solid phase 20, a corresponding amount of converted substrate and a corresponding amount of unconverted substrate.

According to the invention, the reaction is completed in step B6, as the converted substrate solution S' is again removed from solid phase 20 and in step B7 is released to measurement cell M. With this re-pipetting process, the enzymes coupled to the solid phase remain behind. The converted substrate, however, is taken with the solution. Substrate possibly still contained in the solution cannot be further converted, however, since now no enzyme is available in measurement cell M.

As previously described for the clinical chemistry parameters, the enzyme-substrate reaction is evaluated quantitatively in the measurement cell. The optical density of the substrate solution is determined at three different wavelengths. These values are compared with a reference stored in the device or compared with one preset by the operator.

There exists a relation known to one skilled in the art between the time, the amount converted and the reaction temperature. Since the time and reaction temperature are known or preset, then from the converted amount of substrate a retrospective conclusion can be made of the amount of immobilized enzymes and thus of the concentration of the parameter to be determined in the sample p.

If the first factor is finished being determined, then the next reagent cartridge is started. Again initially a determination is made of whether, with the aid of it, a clinical chemistry parameter or an immunodiagnostic one is to be determined. Then again the appropriate one of the two test methods previously described is carried out.

At the conclusion of determining each parameter, the data obtained are passed to a data processing unit, for example a printer, a file or a screen, so that the user can assess and evaluate the data.

If all the desired parameters are determined, all the user needs to do is clean the analysis device while removing the used reagent cartridges RP. Naturally a device is conceivable which ejects the reagent cartridges RP on its own.

If disposable cells were used in carrying out the method, these are also removed. Alternatively, provision can be made that the analysis device be equipped with an automatic cleaning program for the measurement cells M remaining in the device.

The invention is not limited to one of the embodiment forms described previously, but rather is able to be altered in a variety of ways.

All of the features and advantages derived from the specification and drawings, including structural particulars, spatial arrangements and procedural steps, can also be essential to the invention, both per se and in very varied combinations.

It is perceived that in a method for analysis of a sample p, comprising the analysis of clinical chemistry parameters and analysis of immunodiagnostic parameters in a fully automated analysis device, wherein the analysis device comprises a pipetting device, at least one holder for a reagent cartridge RP, which contains the components necessary to carry out the analysis, a holding apparatus for a measurement cell M, at least one measurement cell M, wherein a measurement cell M is assigned to each reagent cartridge RP, a holding apparatus for a sample container P containing sample p, as well as a photometric or spectrometric measuring device, it is especially favorable if the method comprises these steps:
a) Insertion of reagent cartridges RP for the analyses to be carried out into the holding apparatus
b) Insertion of the sample container P containing sample p into the sample device
c) Determining clinical chemistry parameters with the aid of that measurement cell M to which the reagent cartridge RP is assigned, which is provided to carry out the analysis of the particular clinical chemistry parameters, and/or
d) determination of the immunodiagnostic parameters with the aid of that measurement cell M to which the reagent cartridge RP is assigned, which is provided to carry out the analysis of the particular clinical chemistry parameters
e) cleaning or removal of the used measurement cells M
f) removal of the used reagent cartridges RP and the sample container P.

It is advantageous if multiple different clinical chemistry and/or immunodiagnostic parameters are determined from one sample p. For this it is appropriate if, for each clinical chemistry or immunodiagnostic parameter to be determined, a separate reagent cartridge RP is inserted into a holding apparatus for a reagent cartridge RP of the analysis device, with the documenting reagents R1, R2, K, S contained in recesses 12, 13, 14 in the particular reagent cartridge RP for the particular test.

It is further perceived that it is favorable if the reagent cartridges RP which serve for analysis of the clinical chemistry parameters contain at least one documenting reagent R1, R2 and that the reagent cartridges RP, which serve for analysis of the immunodiagnostic parameters, contain a first recess 12 with conjugate K, a second recess 13 with substrate solution S and a solid phase 20, and if the clinical chemistry parameters are determined using the following steps:
a) Taking a documenting reagent R1 from the reagent cartridge RP and taking the sample p with the aid of the pipetting device
g) Releasing the documenting reagent R1 and the sample p from the pipetting device into the measurement cell M assigned to the reagent cartridge RP
h) Incubating the documenting reagent R1 with the sample p, with the documenting reagent R1 reacting with the clinical chemistry parameters present in the sample p to a product that can be photometrically documented
i) Photometric determination of the concentration of the product in the measurement cell M with the aid of the measuring device.

It is also advantageous if the clinical chemistry parameters are determined in the following steps:
a) Taking of a first documenting reagent R1 from a first recess 12 of the reagent cartridge RP and taking of the sample p with the aid of a pipetting device
b) Releasing the documenting reagent R1 and the sample p from the pipetting device into the measurement cell M assigned to the reagent cartridge RP
c) Taking a second documenting reagent R2 from another recess 13, 14 in the reagent cartridge RP with the aid of the pipetting device
d) Releasing the second documenting reagent R2 from the pipetting device into the measurement cell M
e) Incubating the documenting reagents R1, R2 with the sample p, with the documenting reagents R1, R2 reacting with the clinical chemistry parameters present in the sample p to a product that can be photometrically documented
f) Photometric determination of the concentration of the product in the measurement cell M with the aid of the measuring device.

In addition, depending on the desired application, it is advantageous if the clinical chemistry parameters are determined in the following steps:
a) Taking of a first documenting reagent R1 from a first recess 12, 13, 14 of the reagent cartridge RP and taking of the sample p with the aid of a pipetting device
b) Releasing the documenting reagent R1 and the sample p from the pipetting device into the measurement cell M assigned to the reagent cartridge
c) Taking a second documenting reagent R2 from another recess 12, 13, 14 in the reagent cartridge RP with the aid of the pipetting device
d) Releasing the second documenting reagent R2 from the pipetting device into the measurement cell M
e) Taking at least one additional documenting reagent from another recess 12, 13, 14 of the reaction cartridge RP or from a recess 12, 13, 14 of an additional reaction cartridge RP and releasing the additional documenting reagent or reagents to the measurement cell M
f) Incubating the documenting reagent R1, R2 with the sample p, with the documenting reagent R1, R2 reacting with the clinical chemistry parameters present in the sample p to a product that can be photometrically documented
g) Photometric determination of the concentration of the product in the measurement cell M with the aid of the measuring device.

In each case it is favorable if the concentration of the product of the documenting reaction is determined photometrically in the following steps:
Conducting a first photometric measurement in the measurement cell with the aid of the measuring device
Incubating the mixture of the first and/or second documenting reagent and sample in the measurement cell
Conducting a second photometric measurement in the measurement cell with the aid of the measuring device.

One additionally perceives the particular advantage of the invention-specific method that is obtained if the immunodiagnostic parameters are determined by the following steps:
a) Taking of conjugate K from a first recess 12, 13, 14 of the reagent cartridge RP provided for carrying out the immunodiagnostic analysis and taking of a sample p via the pipetting device b) Releasing the conjugate K and sample p from the pipetting device to the solid phase 20 of the reagent cartridge RP
c) Incubating the solid phase 20 with conjugate K and sample p
d) Removal of excess conjugate K and sample p by washing the solid phase 20
e) Taking of substrate solution S from a second recess 12, 13, 14 of the reagent cartridge RP provided for carrying out the immunodiagnostic analysis via the pipetting device
f) Releasing the substrate solution S from the pipetting device to the solid phase 20
g) Incubating the substrate solution S on the solid phase 20
h) Taking of the converted substrate solution S' via the pipetting device
i) Releasing the converted substrate solution S' from the pipetting device into the measurement cell M
j) Measuring the concentration of the converted substrate in the substrate solution S' with the aid of the measuring device.

Overall it is favorable if the method is carried out at a temperature between 27° C. and 39° C., preferably at a temperature of 37° C., and if, after release of the documenting reagent R1, R2, the sample p, conjugate K or substrate solution S, the tip of the pipetting device is changed or cleaned at a washing station.

An additionally very special advantage of the invention comprises a method to determine immunological parameters in a sample p via ELISA in a fully-automated analysis device, wherein the analysis device comprises a holder for a reagent cartridge RP which contains the required components for carrying out the analysis and exhibits a solid phase 20 coupled with antigen or antibodies A, a holding apparatus for a measurement cell M, at least one measurement cell M, with each reagent cartridge RP assigned to a measurement cell M, a holding apparatus for a sample container P containing sample p, and a photometric or spectrometric measuring device, the method comprising these steps:
a) Taking of the conjugate K and sample p via the pipetting device
b) Release of the conjugate K and sample p from the pipetting device to the solid phase 20
c) Incubation of the solid phase 20 with conjugate K and sample p
d) Removal of excess conjugate K and sample p by washing of the solid phase 20
e) Taking of substrate solution S via the pipetting device
f) Release of substrate solution S from the pipetting device to the solid phase 20
g) Incubation of the substrate solution S in the solid phase 20
h) Taking of the converted substrate solution S' via the pipetting device
i) Release of the converted substrate solution S' from the pipetting device into the measurement cell M
j) Measuring the concentration of the converted substrate in the substrate solution S' with the aid of the measuring device.

It is favorable if the conjugate K and the sample p are mixed after release into the solid phase 20, if the concentration is measured by determining the optical density at various wavelengths and/or if, prior to taking of the sample p via the pipetting device in step a), the sample is diluted in a separate dilution cartridge.

LIST OF REFERENCE SYMBOLS

A antigen or antibody
K conjugate
KA carousel
M measurement cell
P sample container
p sample
RP reagent cartridge
R1 documenting reagent
R2 documenting reagent
S substrate solution
S' substrate solution
11 housing
12 recess
13 recess
14 recess
15 recess
20 solid phase

The invention claimed is:

1. A method for analysis of at least one clinical chemistry parameter and at least one immunodiagnostic parameter in a sample using a fully automated analysis device,
wherein the analysis device comprises a pipetting device with a pipetting tip, a photometric or spectrometric measuring device, and a circular carousel for insertion of reagent cartridges and insertion of measurement cells,
wherein each reagent cartridge inserted into the carousel is inserted adjacent to an inserted measurement cell such that each reagent cartridge is paired with a measurement cell, and wherein each reagent cartridge comprises a housing and a first, second and third recess in said housing, the method comprising the steps of:
a) inserting into the carousel a first reagent cartridge and a first measurement cell, the first reagent cartridge and the first measurement cell being positioned adjacent to each other and extending linearly in a radial direction with respect to the circular carousel, wherein the first reagent cartridge comprises reagents necessary to carry out analysis of at least one clinical chemistry parameter;
b) inserting into the carousel a second reagent cartridge and a second measurement cell, the second reagent cartridge and the second measurement cell being positioned adjacent to each other and extending linearly in a radial direction with respect to the circular carousel, wherein the second reagent cartridge comprises reagents necessary to carry out analysis of at least one immunodiagnostic parameter;
c) inserting a sample container containing the sample into a separate holding apparatus in the analysis device;
performing analysis of the at least one clinical chemistry parameter comprising:
d) using the pipetting device to take a first reagent from the first recess of the first reagent cartridge and to take a portion of sample from the sample container;
e) releasing the first reagent and the portion of sample from the pipetting device into the first measurement cell;
f) using the pipetting device to take a second reagent from the second recess of the first reagent cartridge;
g) releasing the second reagent from the pipetting device into the first measurement cell;
h) optionally using the pipetting device to take a third reagent from the third recess of the first reagent cartridge and releasing the third reagent from the pipetting device into the first measurement cell;
g) incubating the reagents and the portion of sample in the first measurement cell to obtain a product;

h) determining the concentration of the product using the photometric or the spectrometric measuring device;

performing analysis of the at least one immunodiagnostic parameter comprising:

i) using the pipetting device to take a conjugate from the first recess of the second cartridge and to take a portion of sample from the sample container;

j) releasing the conjugate and the portion of the sample from the pipetting device into the second recess of the second reagent cartridge, wherein the second recess of the second reagent cartridge contains a solid phase and a substrate solution;

k) incubating the solid phase, the conjugate and the portion of the sample in the second recess of the second reagent cartridge to produce a converted substrate solution;

l) using the pipetting device to take the converted substrate solution from the second recess of the second reagent cartridge;

m) releasing the converted substrate solution from the pipetting device into the second measurement cell;

n) determining the concentration of the converted substrate in the converted substrate solution using the photometric or the spectrometric measuring device.

2. The method of claim 1, wherein multiple different clinical chemistry and immunodiagnostic parameters are determined in the sample.

3. The method of claim 1, wherein the method determines multiple different clinical and immunodiagnostic parameters, and for each clinical chemistry or immunodiagnostic parameter, a different reagent cartridge is inserted into the analysis device, wherein each of the different reagent cartridges contain reagents for the particular parameter.

4. The method of claim 1, wherein after each releasing step, the pipetting tip of the pipetting device is changed or cleaned at a washing station.

5. The method of claim 1, wherein the method is performed at a temperature of 37° C.

6. The method of claim 1, wherein the method is performed at a temperature between 27° C. and 39° C.

* * * * *